(12) United States Patent
Brunnberg et al.

(10) Patent No.: US 8,082,919 B2
(45) Date of Patent: Dec. 27, 2011

(54) DOSE COUNTER DEVICE FOR INHALER

(75) Inventors: Lennart Brunnberg, Tyresö (SE);
Stephan Olson, Stockholm (SE);
Anders Wieselblad, Stockholm (SE)

(73) Assignee: SHL Group AB, Nacka Strand (SE)

( * ) Notice: Subject to any disclaimer, the term of this patent is extended or adjusted under 35 U.S.C. 154(b) by 1025 days.

(21) Appl. No.: 11/915,355

(22) PCT Filed: May 23, 2006

(86) PCT No.: PCT/SE2006/050156
§ 371 (c)(1),
(2), (4) Date: Jan. 7, 2008

(87) PCT Pub. No.: WO2006/126965
PCT Pub. Date: Nov. 30, 2006

(65) Prior Publication Data
US 2008/0210224 A1    Sep. 4, 2008

Related U.S. Application Data

(60) Provisional application No. 60/683,778, filed on May 24, 2005.

(30) Foreign Application Priority Data

May 24, 2005   (EP) .................................... 05104409
Dec. 20, 2005  (SE) .................................... 0502812
Mar. 14, 2006  (SE) .................................... 0600573

(51) Int. Cl.
*A61M 16/00* (2006.01)
*A61M 15/00* (2006.01)
*A61M 11/00* (2006.01)
*A62B 7/00* (2006.01)
*A62B 9/00* (2006.01)

(52) U.S. Cl. .......... 128/200.23; 128/205.23; 128/203.12; 128/203.15; 128/200.14; 128/200.24

(58) Field of Classification Search .......... 128/200.11–200.24, 203.12, 203.15, 128/205.23; 222/36, 38, 48, 162, 32, 33, 222/402.13, 402.11, 402, 13; 116/285, 312, 116/315, 308, 318, 311; 215/230; 206/459.1, 206/459.5; 604/58
See application file for complete search history.

(56) References Cited

U.S. PATENT DOCUMENTS 5,421,482 A  *  6/1995  Garby et al. .................... 222/36
(Continued)

FOREIGN PATENT DOCUMENTS

| EP | 0 254 391 A1 | 1/1988 |
| EP | 1131248 | 9/2001 |
| FR | 2857769 A1 | 1/2005 |

(Continued)

OTHER PUBLICATIONS

PCT International Search Report and written opinion, mailed Aug. 2, 2006, in connection with International Application No. PCT/SE2006/050156.

*Primary Examiner* — Annette Dixon
(74) *Attorney, Agent, or Firm* — Potomac Patent Group PLLC

(57) ABSTRACT

A dose counter device for an inhaler that in a reliable way registers a delivered dose from a canister in the inhaler and that at the same time substantially reduces the risk of falsely registering a dose not delivered substantially avoids erroneous counting of delivered doses from the canister.

16 Claims, 14 Drawing Sheets

U.S. PATENT DOCUMENTS

| | | | |
|---|---|---|---|
| 6,082,358 A * | 7/2000 | Scarrott et al. | 128/205.23 |
| 7,191,918 B2 * | 3/2007 | Ouyang et al. | 222/36 |
| 7,464,708 B2 * | 12/2008 | Marx | 128/205.23 |
| 7,568,481 B2 * | 8/2009 | Scarrott et al. | 128/205.23 |
| 7,780,038 B2 * | 8/2010 | Ingram et al. | 222/36 |
| 7,882,982 B2 * | 2/2011 | Stradella et al. | 222/38 |
| 2004/0149773 A1 | 8/2004 | Ouyang et al. | |

FOREIGN PATENT DOCUMENTS

| | | |
|---|---|---|
| WO | 98/28033 A1 | 7/1998 |
| WO | 99/57019 A2 | 11/1999 |
| WO | 03/086518 A1 | 10/2003 |
| WO | 2005/007226 A1 | 1/2005 |
| WO | 2006/004496 A1 | 1/2006 |

* cited by examiner

DOSE COUNTER DEVICE FOR INHALER

This application is a national-phase application under 35 USC 371 of International Application PCT/SE06/50156 filed on May 23, 2006, and a non-provisional of U.S. Provisional Patent Application No. 60/683,778 filed on May 24, 2005.

TECHNICAL FIELD

The invention refers to a dose counter device for an inhaler that in a reliable way will register a delivered dose from a canister comprised in the inhaler, and that at the same time will substantially reduce the risk of falsely register a dose not delivered. Thus, the present invention will in an effective way, substantially avoid erroneous counting of delivered doses from the canister.

PRIOR ART

Within the field of inhalers, dose counters are known that will count the number of doses delivered from a canister comprised in the inhaler. The user will thus for instance know the number of doses taken or the number of doses remaining in the canister.

A problem with known dose counters is that they at times will register a delivered dose that never was delivered, and that they also may miss to register a dose that in fact was delivered. The user of the inhaler is thus provided with false information about the number of doses remaining in the inhaler, which may constitute a major problem for instance an asthmatic person which thus unintentionally may run out of medicament.

In EP-A2-0966309, a dose counter is located near the valve region of the canister and attached to the base of an actuator, wherein the displacement of the top of the canister relative to the valve stem is measured.

In EP-A1-0254391, a dose counter is located on the top of the inhalation device, wherein the displacement of the top of the canister relative the actuator body is measured.

Since canisters suffers from manufacturing height dimension variations and the counters in EP-A2-0966309 and in EP-A1-0254391 works taking into account the displacement of the canister, there exist a great risk for having counting errors.

In EP-A2-1131248, a dose counter is located on the top of the inhalation device, wherein the dose counter counts when a given pressure of a spring is achieved, such that the counting is achieved before a dose is given. A drawback with such a counter is that the force of the spring and the counting means must be accurately controlled.

Therefore, there is a general need for a dose counter device that in a reliable way will register a delivered dose from a canister comprised in the inhaler, and that at the same time substantially will reduce the risk of falsely register a dose not delivered. As understood, it is very difficult, if not impossible; to construe a device that registers the in fact delivered dose with 100% accuracy. However, from the users' point of view, it is better to have at hand a dose counter device that occasionally may register a dose delivery even though no dose was in fact delivered, than to have it the other way around. In this way, the user can not unintentionally run out of medicament.

Further, such a dose counter is known in WO-A1-2006/004496, which discloses a dose counter that is attached and pressed down to a canister in an assembling process until the height of the counter and the canister together is within a predetermined height. The counting is related to the downward motion of the canister and the counter. The combination (dose counter attached and pressed down to a canister) interacts with the valve means of the housing. A drawback with such a counter is that it only compensates for the canisters' manufacturing height dimension variations without taking into account either the manufacturing height dimension variations of the dose counter means or the height dimension variations of the arrangement between the canister and the inhaler housing, which have also the potential to cause miscounting.

SUMMARY

The aim of the present invention is therefore to provide a dose counter device that satisfies the above described need.

This aim is solved by the present invention characterised by claim 1. Additional advantageous developments of the present invention are characterised by the dependent claims.

According to one major aspect of the invention, there is provided a dose counter device for an inhaler adapted to be mounted on the distal end of the inhaler, said inhaler comprises an arrangement wherein a canister is comprised in an inhaler housing, wherein the distal end of the canister protrudes a distance from the distal end of the inhaler housing, and wherein said housing and said distal end of the canister interact with dose counter means to register a delivered dose, wherein the dose counter device is provided with means arranged and designed to calibrate for height dimension variations of said canister, of said dose counter means and of said arrangement and to interact with said counter means to register a delivered dose.

This solution provides the advantage that an erroneous counting of the delivered dose from the canister caused by the height dimension variations of said canister, of said dose counter means and of said arrangement is avoided.

DETAILED DESCRIPTION OF THE INVENTION

Figure 1:
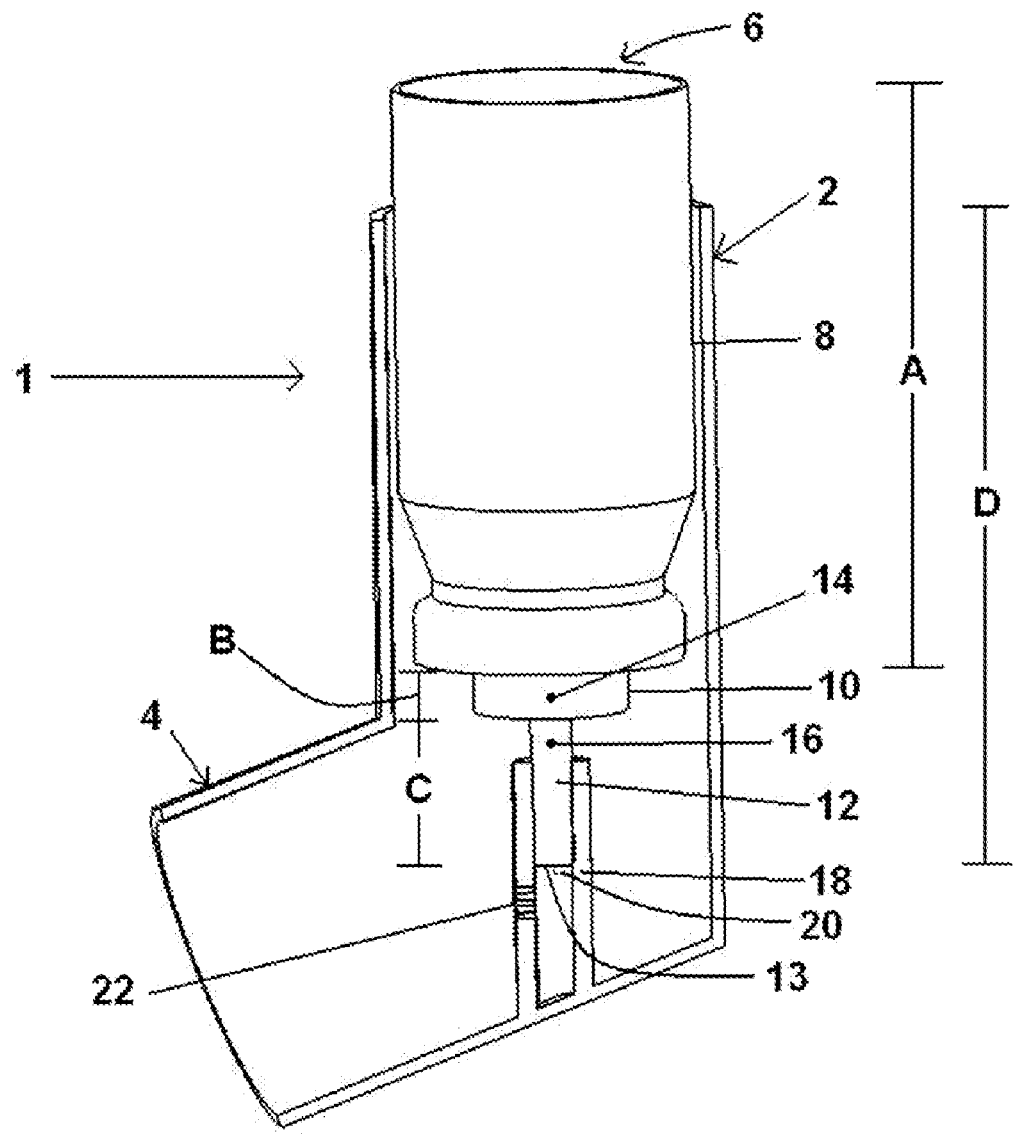
FIG. 1 illustrates a general inhaler comprising a liquid medicament containing canister, when the inhaler is in a non-activated state.

With reference to FIG. 1, a general inhaler 1 comprises a housing 2 having a mouthpiece 4, which the user puts in his mouth when a dose of medicament is to be inhaled. The housing 2 of the inhaler is adapted to receive a standard canister 6, containing liquid medicament, wherein the distal end of the canister 6 protrude a certain distance from the distal end of the housing 2. The canister comprises a main canister body 8 that is adapted to communicate with a dose chamber 10. The dose chamber 10 is in turn provided with a hollow spring-suspended transfer tube 12 provided with an outlet 13 in its proximal end. The dose chamber is further provided with an outlet valve 14 that is adapted to correspond to a valve 16 in the transfer tube 12. The interior of the mouthpiece 4 is provided with a tubular receiving means 18, having an inward protruding flange 20, provided a predetermined distance from the bottom of the receiving means 18. The receiving means 18 is further provided with an outlet 22 that communicates with the outlet of the mouthpiece 4.

The proximal end of the transfer tube 12 abuts against the flange 20, such that a part of the outlet 13 of the transfer tube communicates with the outlet 22 of the receiving means.

When a user of the inhaler intends to inhale a dose, he puts the mouthpiece in his mouth and applies a force, generally by the aid of his hand and fingers or the like, on the distal surface of the canister 6, such that the canister body 8 and the dose chamber 10 is forced downwards towards the bottom of the housing 2, i.e. towards the proximal end of the canister, while the transfer tube 12 remains still. Thus, when the dose chamber 10 has moved a predetermined distance towards the bottom of the housing, the valve 16 of the transfer tube 12 will open communication with the valve 14 of the dose chamber, such that a metered dose of the pressurised liquid medicament contained in the main body 8 will flow from the dose chamber 10, through the valves 14, 16, the transfer tube 12, the outlets 13, 22 and out through the outlet of the mouthpiece 4. When the user releases the force applied to the distal end of the canister, the canister will move back to its original position.

The distance between the valves 14, 16 is a known predetermined distance, generally 2 mm, when the inhaler is in the first non activated state, i.e. the dose chamber needs to in a second activated state be forced downwards with a distance of 2 mm for the valves 14, 16 to open communication with each other. It would be a simple case to construe a reliable dose counter device if the dimensions of the inhaler, would be exact dimensions. However, all dimensions of the general inhaler, such as the height of the main body A, the height of the dose chamber B, the length of the transfer tube C, the distance between the proximal end of the transfer tube and the distal edge of the housing D and the height of the dose counter means, are impaired by variation of not neglectable magnitude. If for instance the variation of the distances A, B, C, D is ±0.4 mm, ±0.05 mm, ±0.25 mm, ±0.2 mm, respectively and the variation of height of dose counter means is ±0.1 mm, the sum of all margins of errors will be ±1 mm. So, if one for instance construes a dose counter device that determines the distance that the canister has moved towards the bottom of the housing, dependent on a single reference point, for instance the distal edge of the housing 2, and register a delivered dose when said distance amount to 2 mm, the dose may or may not have been delivered. Also, the dose may have been delivered without the distance amounting to 2 mm.

The solution to this problem, is according to a first and a second embodiment of the present invention an all mechanical solution, and is based on the idea, that during manufacturing of the dose counter device one establishes a fix known reference point, or reference distance that permits to determine an accurate distance that the canister has to be displaced within an inhaler before a delivered dose is registered. This offers a dose counter that compensates for the height dimension variations of the canister, the means of the dose counter and the arrangement between the canister and the inhaler housing, whereby erroneous counting of delivered doses from the canister is avoided.

Figure 2:
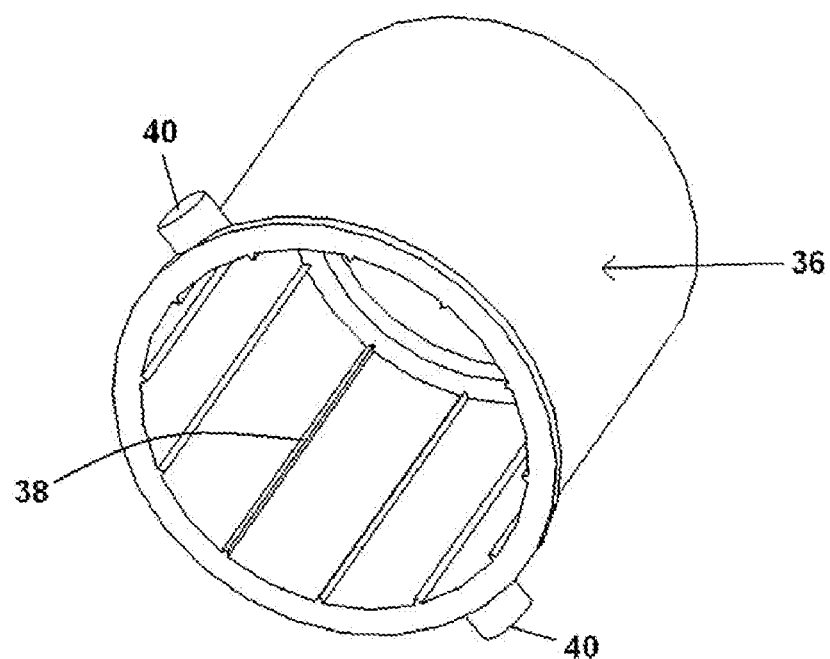
FIG. 2 illustrates a calibrating means of the present invention.

In FIG. 2 is shown a calibrating means 36 of the dose counter device, having a sleeve-formed configuration. The interior of the calibrating means has inward preferably equally distributed protruding ribs 38 extending along the longitudinal axis of the means 36. The ribs 38 preferably have a triangular shape and are manufactured of an easily deformable plastic material. The outer surface of the proximal end of the means 36 is provided with preferably two equally distributed outward protruding pins 40.

Figure 3:
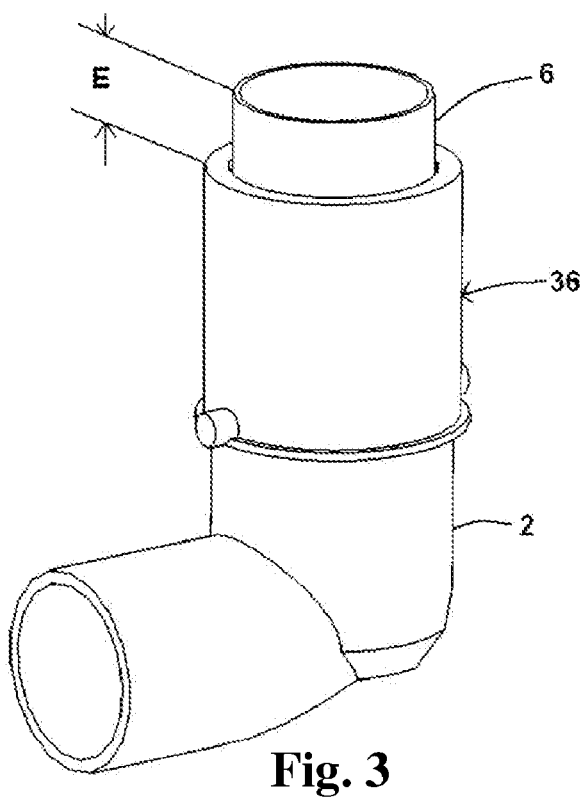
FIG. 3 illustrates the calibrating means of FIG. 2, mounted on top of the inhaler.

The calibrating means 36 is adapted to be mounted over the distal end of the inhaler housing 2, as seen in FIG. 3. The ribs 38 will during this mounting procedure deform and break and the calibrating means will thus be tightly and not removably fitted on the inhaler housing 2. This mounting procedure is a well controlled process so that the distance between the distal end of the calibrating means 36 and the distal end of the canister 6, when the mounting procedure is finished, is a well defined and predetermined distance, indicated in FIG. 3 by the letter E.

Figure 4:
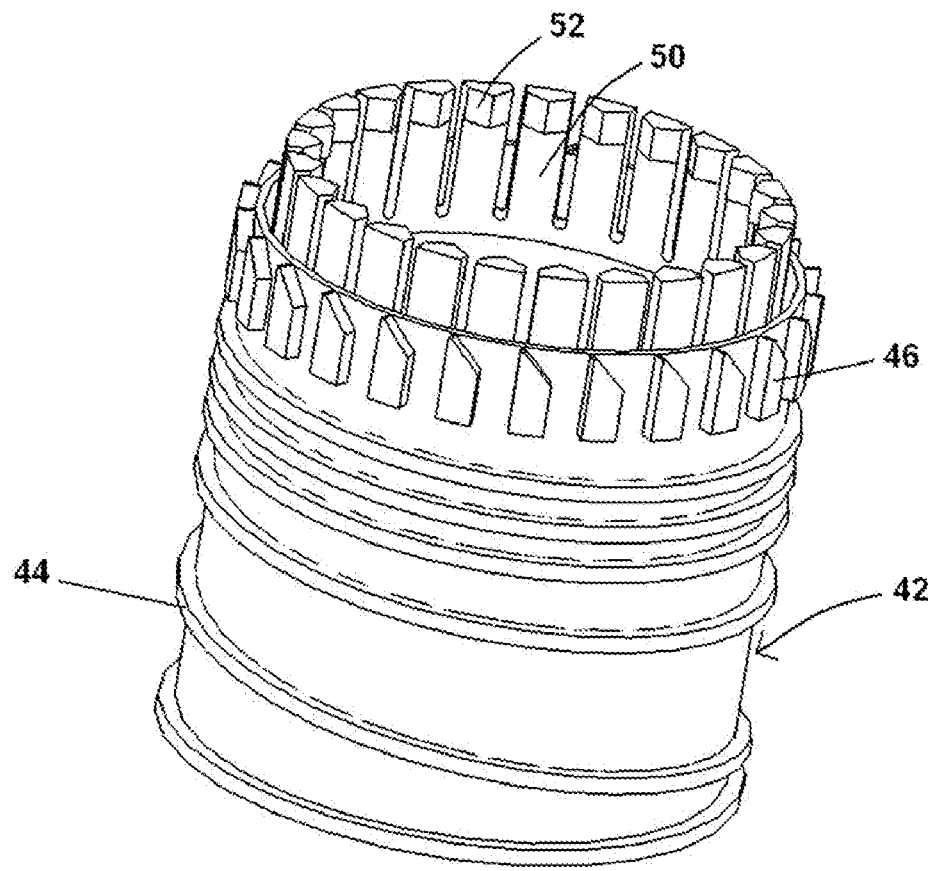
FIG. 4 illustrates a driving means of the present invention according to a first embodiment.

In FIG. 4 is shown a component adapted to be used in the present invention according to a first embodiment. Said component is a driving means 42 having a sleeve-formed configuration designed in accordance with the calibrating means 36. The interior surface of the means 42 is at its proximal end provided with a means (not shown) that corresponds to a means (not shown) on the exterior surface at the proximal end of the calibrating means, so that the driving means is adapted to be fitted over the calibrating means and at a place adapted to be rotated but not be movable along the longitudinal axis of the calibrating means.

The exterior surface of the driving means 42 is further provided with a thread 44, preferably having a variable pitch of grooving. As seen in FIG. 4, the pitch of grooving is finer towards the distal end of the driving means. The exterior surface of the distal end of the driving means is further provided with a number of equally distributed pins 46 having a bevelled edge at their distal end. The driving means is further at its distal end provided with upward protruding pins 50. The pins 50 are at their distal end provided with triangularly shaped teeth 52 protruding towards the interior of the driving means.

Figure 5:
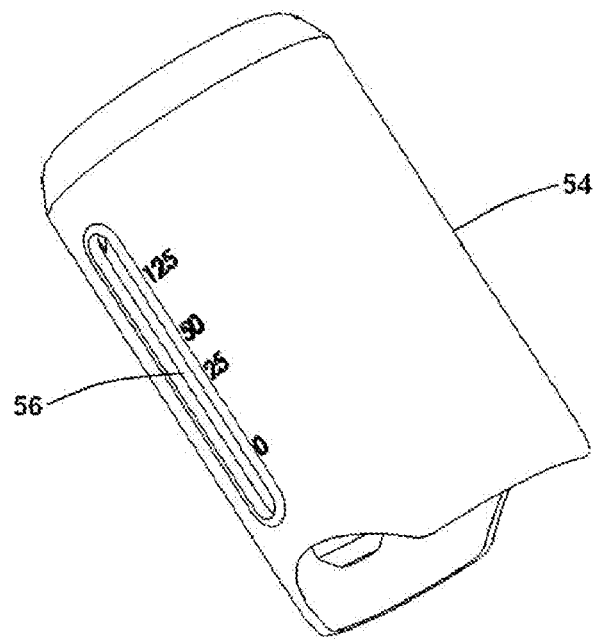
FIG. 5 illustrates a house of the present invention.

The driving means 42 of the first embodiment is adapted to be fitted in the interior of a house 54 shown in FIG. 5. The house is provided with a dose window 56, and means that corresponds to the pins 40 of the calibrating means. In order for the driving means 42 to be fitted in the house 54, the inner surface of the distal end of the house is thus provided with a means that corresponds to the means provided on the distal end of the driving means. So when the dose counter device according to the first embodiment is to be used, the driving means 42 is mounted in the interior of the house 54, and the two components are mounted over the calibrating means already fitted with the inhaler housing, see FIG. 6.

Figure 6:
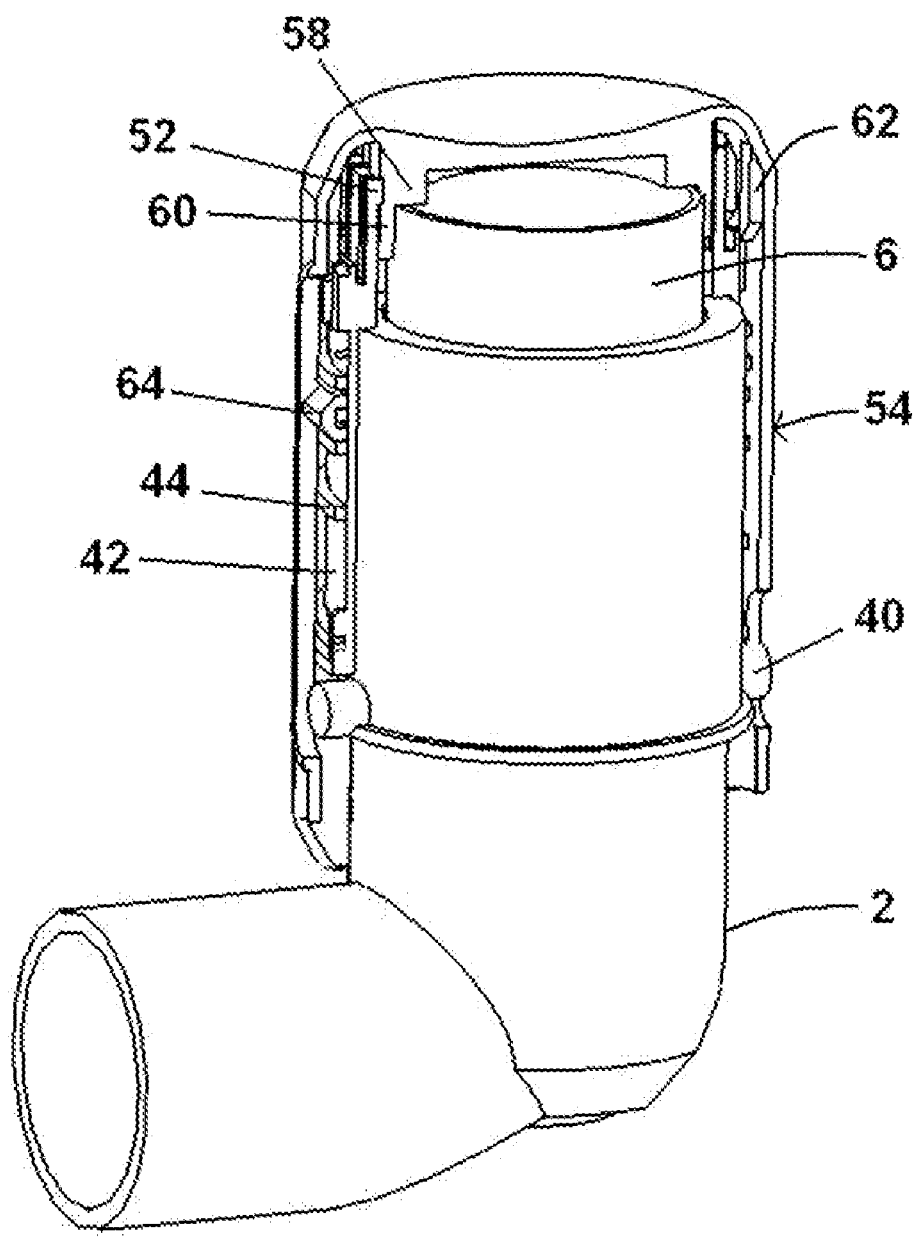
FIG. 6 illustrates the components of FIG. 2-5 mounted on top of an inhaler according to a first embodiment, partly seen in cross-section

In FIG. 6 it is shown that the interior surface at the distal end of the house 54 is provided with a downward protruding flange 58, adapted to be in contact with the distal end of the canister 6. That is, when the dose counter is mounted and ready for use, the distance between the distal end of the calibrating means and the distal end of the canister 6, i.e. the proximal edge of the flange 58 and the distal end of the calibrating means is a known predetermined distance, i.e. the distance E.

Figure 7:
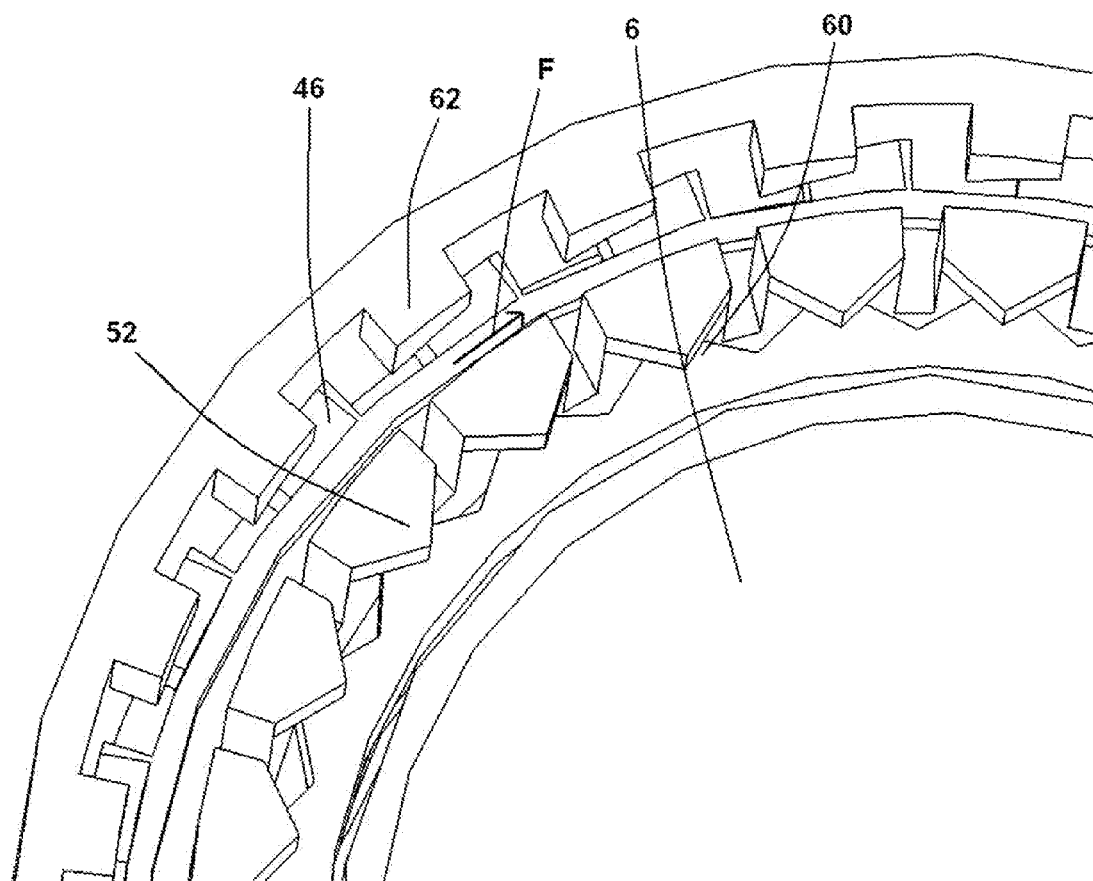
FIG. 7 illustrates the distal end of the dose counter device according to the first embodiment mounted on top of an inhaler, as seen in cross-section from above.

When the user of the inhaler intends to inhale a dose, he applies a force on the distal end of the house 54, which thus moves towards the proximal end of the canister. The flange 58 will thus urge the canister downwards. The flange 58 is further provided with outwardly protruding triangularly shaped teeth 60, which correspond to the teeth 52 of the driving means, as seen in FIG. 6 and in FIG. 7, wherein the latter illustrates a cross section of the distal end of the dose counter device when mounted on top of an inhaler. The interior surface of the distal end of the house is further provided with inward protruding pins 62 having a bevelled edge at their proximal end that corresponds to the bevelled edge of the pins 46 on the driving means. When thus the house 54 is urged downwards, the bevelled edge of the pins 62 will move along the bevelled edge of the pins 46 and urge the driving means to rotate in the direction indicated by the arrow F in FIG. 7. Since the height between the proximal end of the flange 58 and the distal end of the calibrating means is a known distance, i.e. the distance E, the dose counter device is so designed that the distance that one tooth 52 has to move in order to for its tip to meet the tip of a tooth 60 of the house 54 is a known predetermined distance that corresponds to a predetermined distance that the canister body then has moved towards the proximal edge of the inhaler. In this particular embodiment said distance is 1 mm. This is due to the fact that, when the user has pressed the canister downwards this particular distance, one can be pretty certain that he is to inhale a dose and that the downward movement of the canister was not as a result of general handling of the inhaler. Thus, when the two tips of the teeth 52, 60 meet, the tooth 52 will inevitably slide over the tooth tip 60 and the dose counter device has thus rotated one step and has accordingly registered a delivered dose. A more detailed description of the cooperation between the pins 46 and 62 is provided below in connection with the FIGS. 10-12.

The driving means is thus rotated one step when the house is applied with a force on its distal end that will urge a tooth 52 to slide over a tooth 60. A dose indicating means 64 is provided over the thread 44 but provided in the dose window 56. The means 64 thus rides along the thread when the driving means is rotated and moves down towards the proximal end of the dose window, indicating the dose remaining in the canister. In FIG. 5, the dose scale is seen provided as a progressive scale that corresponds to the variable pitch of grooving of the thread, but naturally the thread can have a non-variable pitch of a grooving, that corresponds to a non-progressive dose scale.

Preferably spring means (not shown) is provided between the inner distal end of the house and the distal end of the canister so that the house springs back towards the distal end of the inhaler when the user releases the force applied to the distal end of the house.

According to a second embodiment of the present invention, the driving means and the interior of the house have slightly different configurations. In the following description of the second embodiment of the invention, components having essentially the same function as in the first embodiment but having a different configuration, have been designated the same reference number as in the first embodiment followed by a '-sign. Components having essentially the same function and also essentially the same configuration, have accordingly been designated the same reference number as in the first embodiment. New components have naturally been designated new reference numbers.

Figure 8:
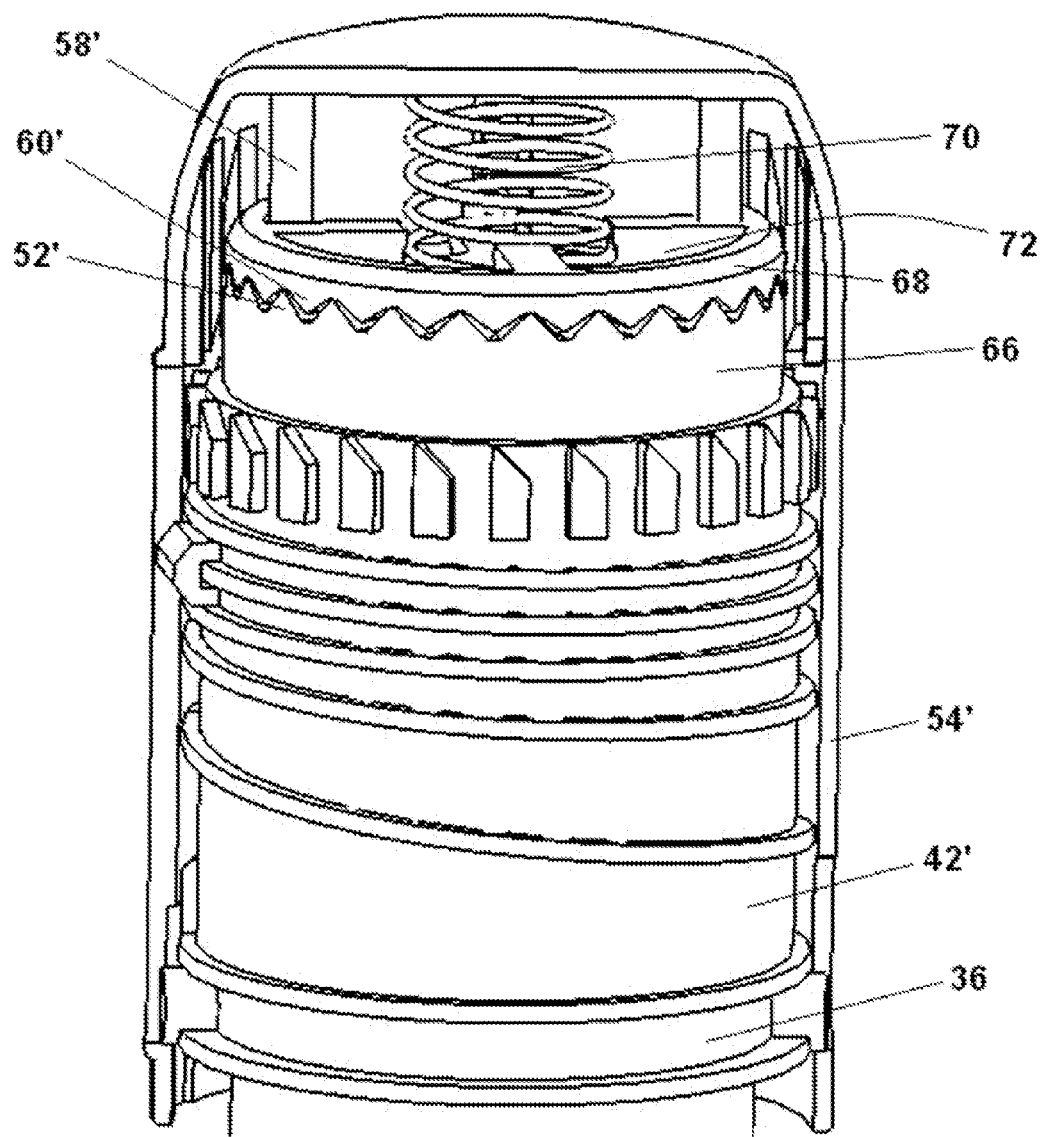
FIG. 8 illustrates the components of the dose counter device according to a second embodiment mounted on top of an inhaler in a non-activated state, partly seen in cross-section.

The driving means of the second embodiment, seen in FIG. 8, has thus accordingly been designated the reference number 42'. The driving means 42' is adapted to be mounted over the calibrating means 36 as in the first embodiment. The difference between the driving means of the first and second embodiment, respectively, can be seen at the distal end of the driving means. Instead of having the upward protruding pins 50, provided with the inwardly protruding triangularly shaped teeth 52, the driving means 42' is provided with an upward protruding crown 66. The crown is in turn on its distal edge provided with equally distributed upwardly protruding triangularly shaped teeth 52'.

As in the first embodiment, the driving means 42' is adapted to be fitted inside the house 54'. The difference between the house of the first and the second embodiment, respectively, is that no outward protruding triangularly shaped teeth 60 are provided in the house 54'. Instead, a non-rotating means 68 is provided in the distal end of the interior of the house 54', overlaying the driving means 42' and the crown 66. The proximal edge of the non-rotating means is provided with downward protruding triangularly shaped teeth 60', that correspond to the teeth 52' of the driving means 42'.

Figure 14:
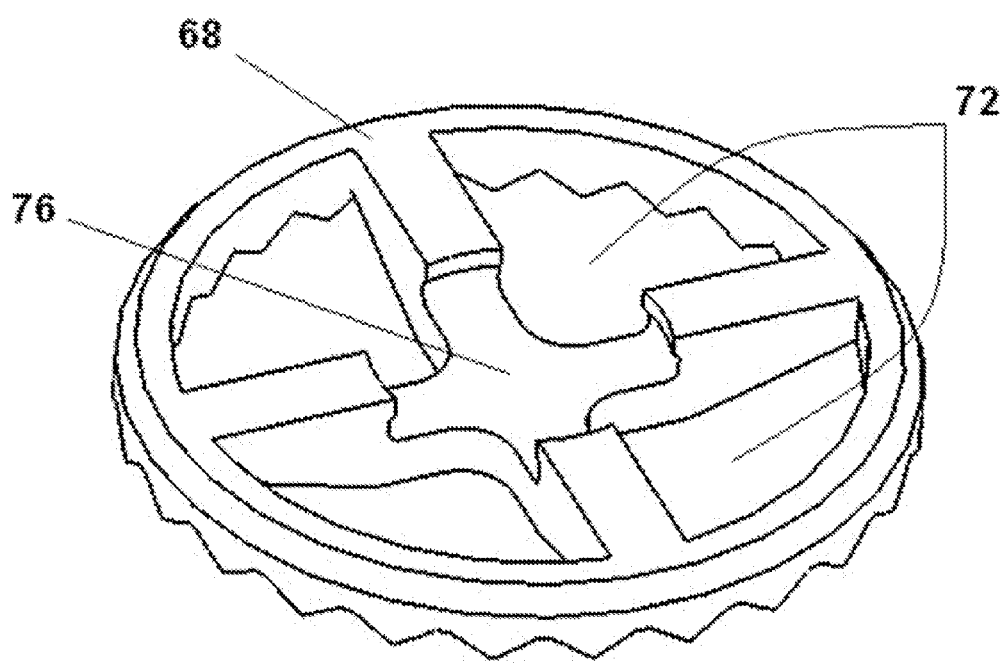
FIG. 14 illustrates in an elevated view a non-rotating means according to the second embodiment.

The non-rotating means is provided as being suspended by a spring 70. The spring 70, preferably a helical steel spring is thus mounted between the inner distal surface of the house 54' and the top of the non-rotating means. The non-rotating means 68 is not provided as a solid means but is provided with through going openings 72. The number of openings 72 is in this particular embodiment four, such that the non-rotating means 68 when seen from above as in FIG. 14, can be seen as a means having a circular circumference provided with the openings 72 in the interior of the means. The demarcations between said openings thus constitute a cross-like shape. The spring 70 is thus provided as to operate between the centre of the cross 76 and the centre of the distal inner surface of the house 54'. The downward protruding flange 58' of the house 54' is thus designed in accordance with the non-rotating means 68, such that when it is forced towards the proximal end of the inhaler, it is adapted to come in contact with the distal edge of the canister through the openings 72 of the means 68.

Figure 9:
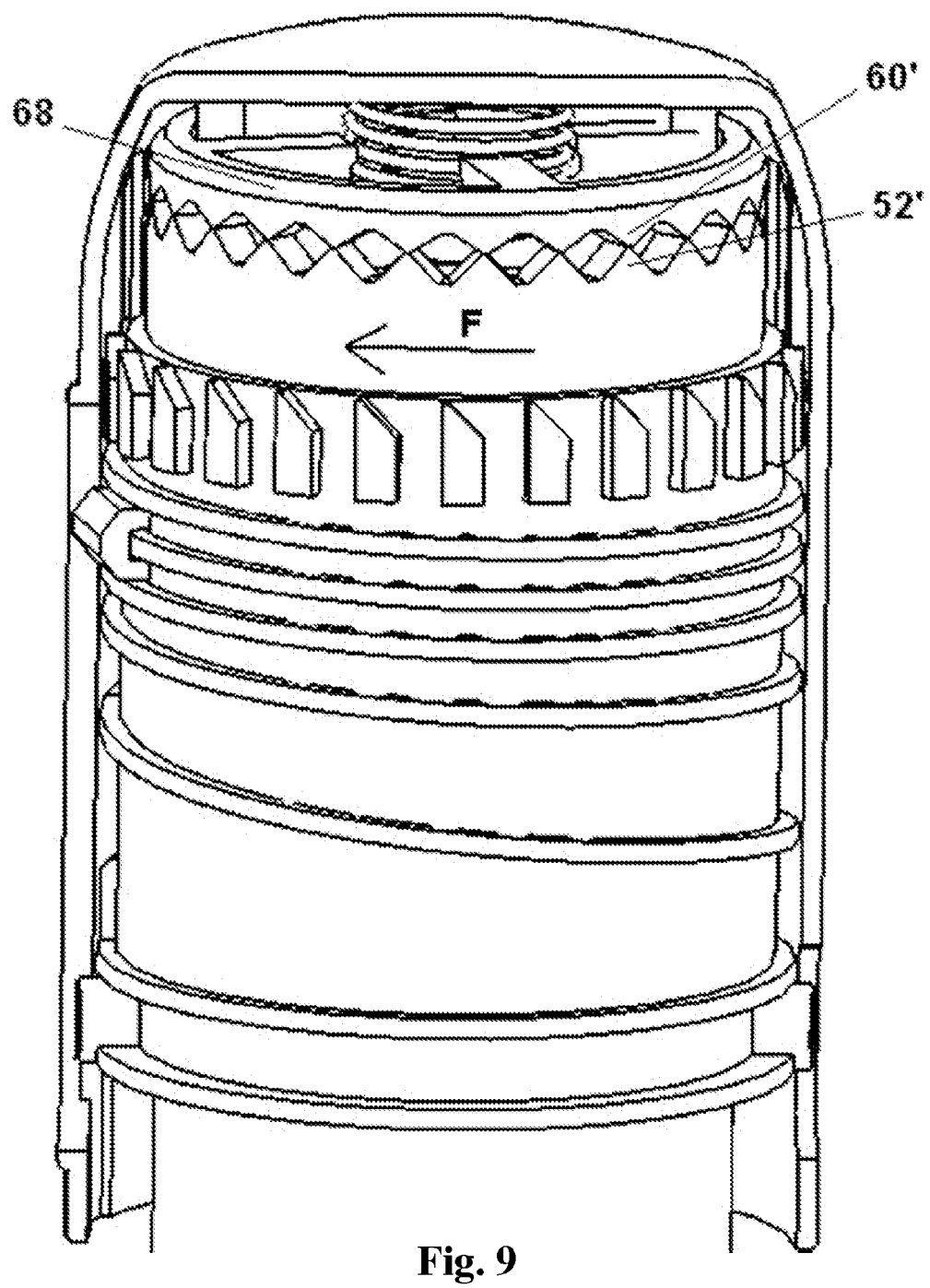
FIG. 9 illustrates the dose counter device as seen in FIG. 8 but in an activated state.

So, in the second embodiment when thus the house 54' is urged downwards, the bevelled edge of the pins 62 of the house 54' will move along the bevelled edge of the pins 46 and urge the driving means to rotate in the direction indicated by the arrow F in FIG. 9. The movement of the driving means to the left as seen in FIG. 9, will thus result in that a tip of a tooth 52' also will move to the left urging the spring-suspended non-rotating means 68 up towards the distal end of the inhaler. Since the height between the proximal end of the flange 58' and the distal end of the calibrating means is a known distance, i.e. the distance E, the dose counter device is so designed that the distance that one tooth 52' has to move in order to for its tip to meet the tip of a tooth 60' is a known predetermined distance and that corresponds to a predetermined distance that the canister body then has moved towards the proximal edge of the inhaler. When a tip of a tooth 52', meets a tip of a tooth 60', the canister body has in this particular embodiment moved 1 mm towards the proximal end of the inhaler. This is due to the fact that when the user has pressed the canister downwards this particular distance, one can be pretty certain that he is to inhale a dose and that the downward movement of the canister was not as a result of general handling of the inhaler. Thus, when the two tips of the teeth 52', 60' meet, the tooth 52' will inevitably slide over the tooth tip 60' and the dose counter device has thus rotated one step and has accordingly registered a delivered dose, as described in connection with the first embodiment.

Figure 10:
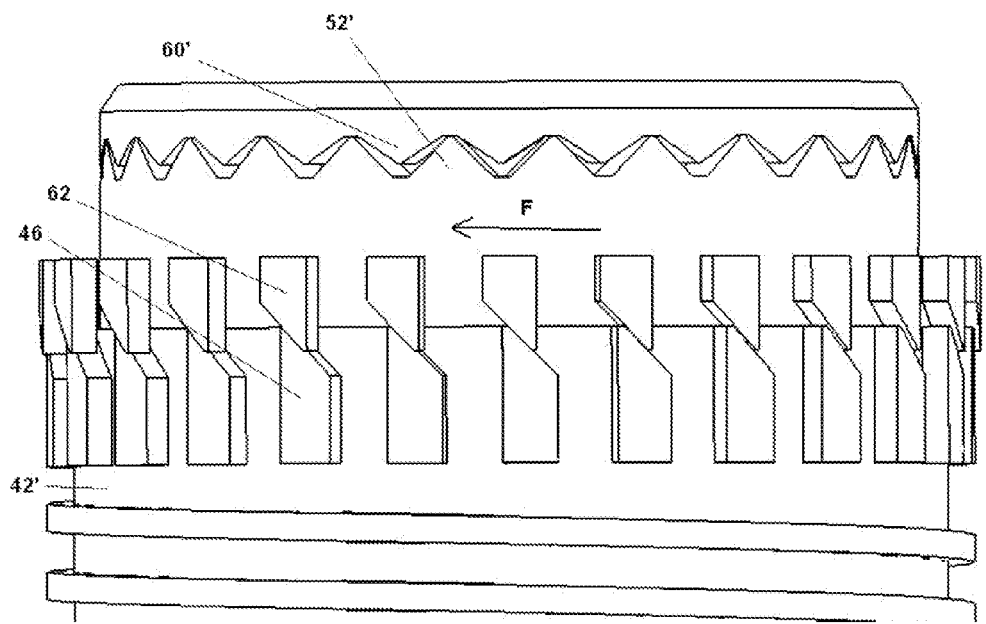
FIG. 10-12 illustrates the cooperation between the house and the driving means in three different subsequent stages of the activated state.
Figure 11:
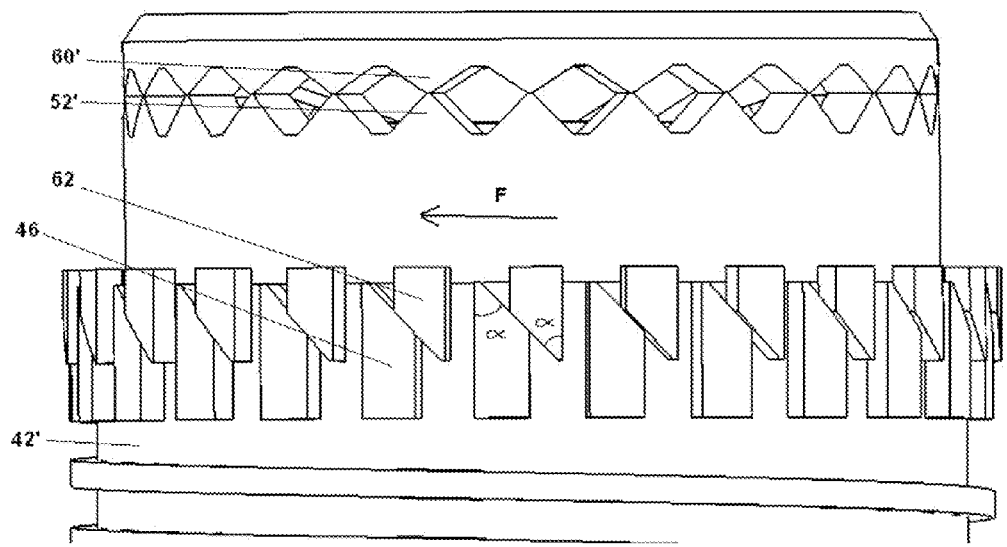
Figure 12:
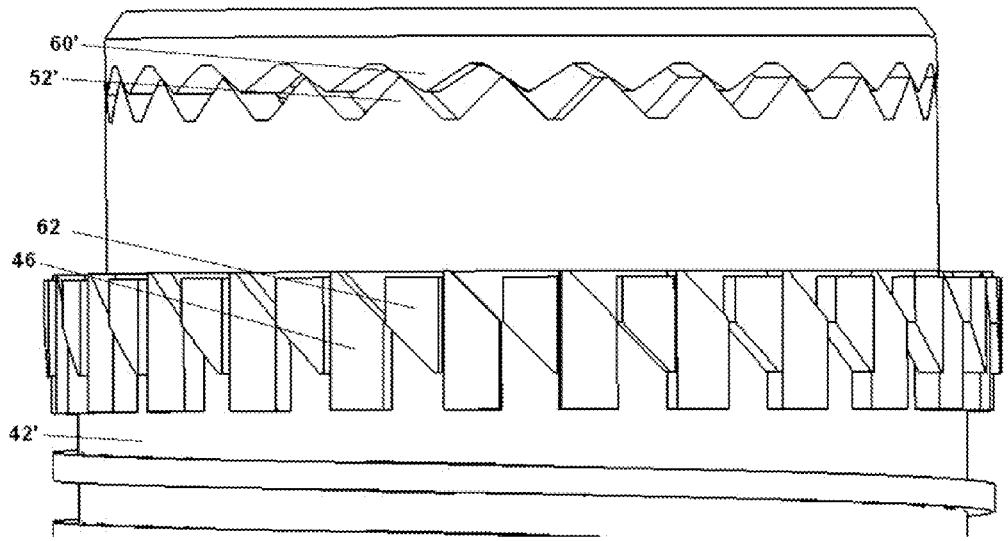

In FIGS. 10-12, is seen the cooperation between the inward protruding pins 62 of the house 54, 54' and the pins 46 on the driving means 42, 42'. The cooperation between the pins 62 and the pins 46 is the same in the first and the second embodiment, respectively, that is, said figures can be read also in connection with the first embodiment even though the non-rotating means 68 and its cooperation with the driving means 42' is illustrated in the figures. Now turning to FIG. 10; when the house 54, 54' is urged downwards, the bevelled edge of the pins 62 will move along the bevelled edge of the pins 46 and thus urge the driving means to rotate in direction indicated by the arrow F. In FIG. 11 is shown when the tip of a 52' has met the tip of a tooth 60', i.e. the non-rotating means is rotationally fixed but is moved towards the distal end of the canister against the spring force 70 as the tooth tip 52' moves in the direction F. The distance that one tooth tip 52, 52' has to move in order to meet a tooth tip 60, 60' is designed so that it is in conformity with the predetermined distance that the pins 62 move towards the proximal end of the inhaler until a dose is registered as delivered, in this particular embodiment 1 mm. This is accomplished by for instance providing the bevelled edge of the pins 46 and 62 with the correct inclination, i.e. the correct value of the angle α.

In FIG. 12 is shown when one tooth tip 52' has slid passed the tooth tip 60', with which tip it was previously in contact with. Due to the spring 70, the non-rotating means will now be urged back downwards to its original position. As previously mentioned, when one tooth tip 52, 52' has slid passed its corresponding tooth tip 60, 60' a dose is registered as delivered. The user however, continues to urge the house and thus the canister towards the proximal end of the inhaler until the dose is actually delivered. The user then releases the force applied to the distal end of the house 54, 54', whereupon the canister and the house will move back to their original positions. Due to the one step rotation of the driving means 42, 42', a pin 62 will the next time a dose is to be delivered, cooperate with the pin 46 following the pin it just previously cooperated with.

Figure 13:
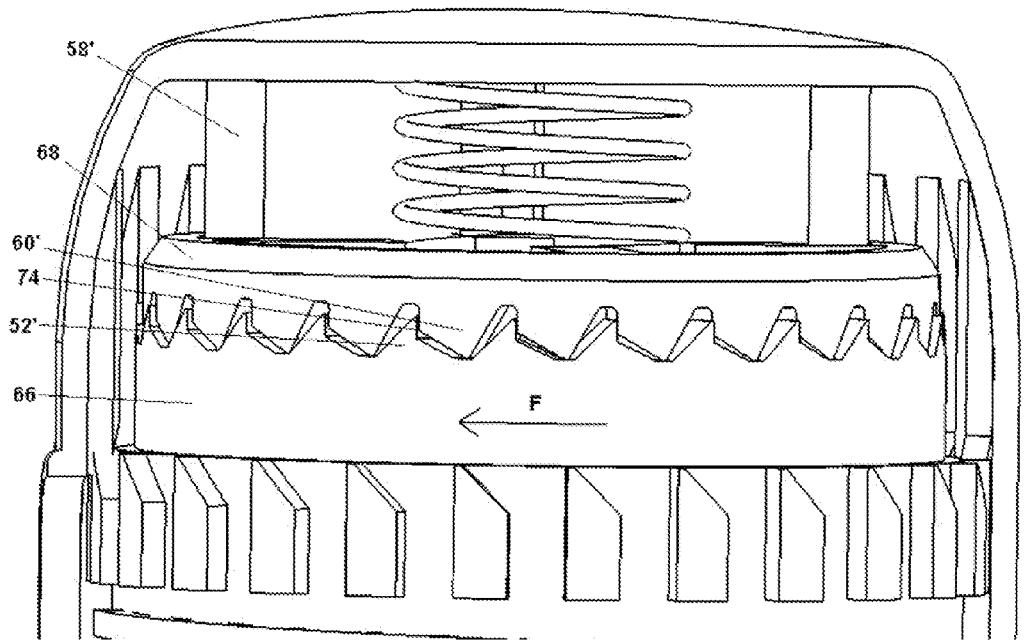
FIG. 13 illustrates means of the dose counter device that prevent the driving means to be rotated in the wrong direction.

The dose counter device is further preferably provided with means that prevent that the driving means is rotated in the wrong direction, which will result in a wrongful indication about the remaining doses in the canister. In FIG. 13 is seen one embodiment of such wrong rotation direction preventing means 74. The means 74 is here illustrated and described in connection with the second embodiment but as the skilled person readily understands, such means 74 can with minor adjustments very well be functional also with the first embodiment.

In FIG. 13, the wrong rotation direction preventing means 74 can be seen as a slightly different configuration of the teeth 52'. The sides of teeth in line with the rotation direction F are unchanged. The other sides of the teeth however, do no longer have an even slope, but are provided with an upward protruding edge 74, i.e. the teeth 52' no longer have a triangular shape but the shape as seen in FIG. 13. The distal tip of the edge 74 now takes over the function of the tip of the tooth 52'. The driving means 42' is in an effective way prevented to be rotated in the direction opposite to the direction F by means of the edge 74. That is, a tooth 60' can not slid pass such an edge 74 if the driving means is rotated in the direction that is opposite the rotation direction F.

Further, the solution to the mentioned problem in the introduction part, is according to a third embodiment of the present invention an all mechanical solution, and is based on the idea, that an actuating means, when depressed, travels a longitudinal distance until it makes contact with the distal end of the canister, to then interact with an intermediate means before a dose counter registers a delivered dose. This offers a dose counter that compensates automatically for the height dimension variations of the canister, the means of the dose counter and the arrangement between the canister and the inhaler housing, whereby erroneous counting of delivered doses from the canister are avoided.

According to a third embodiment of the present invention, the driving means and the interior of the house have slightly different configurations. In the following description of the third embodiment of the invention, components having essentially the same function as in the second embodiment but having a different configuration, have been designated the same reference number as in the second embodiment followed by a "-sign. Components having essentially the same function and also essentially the same configuration, have accordingly been designated the same reference number as in the second embodiment. New components have naturally been designated new reference numbers.

Figure 15:
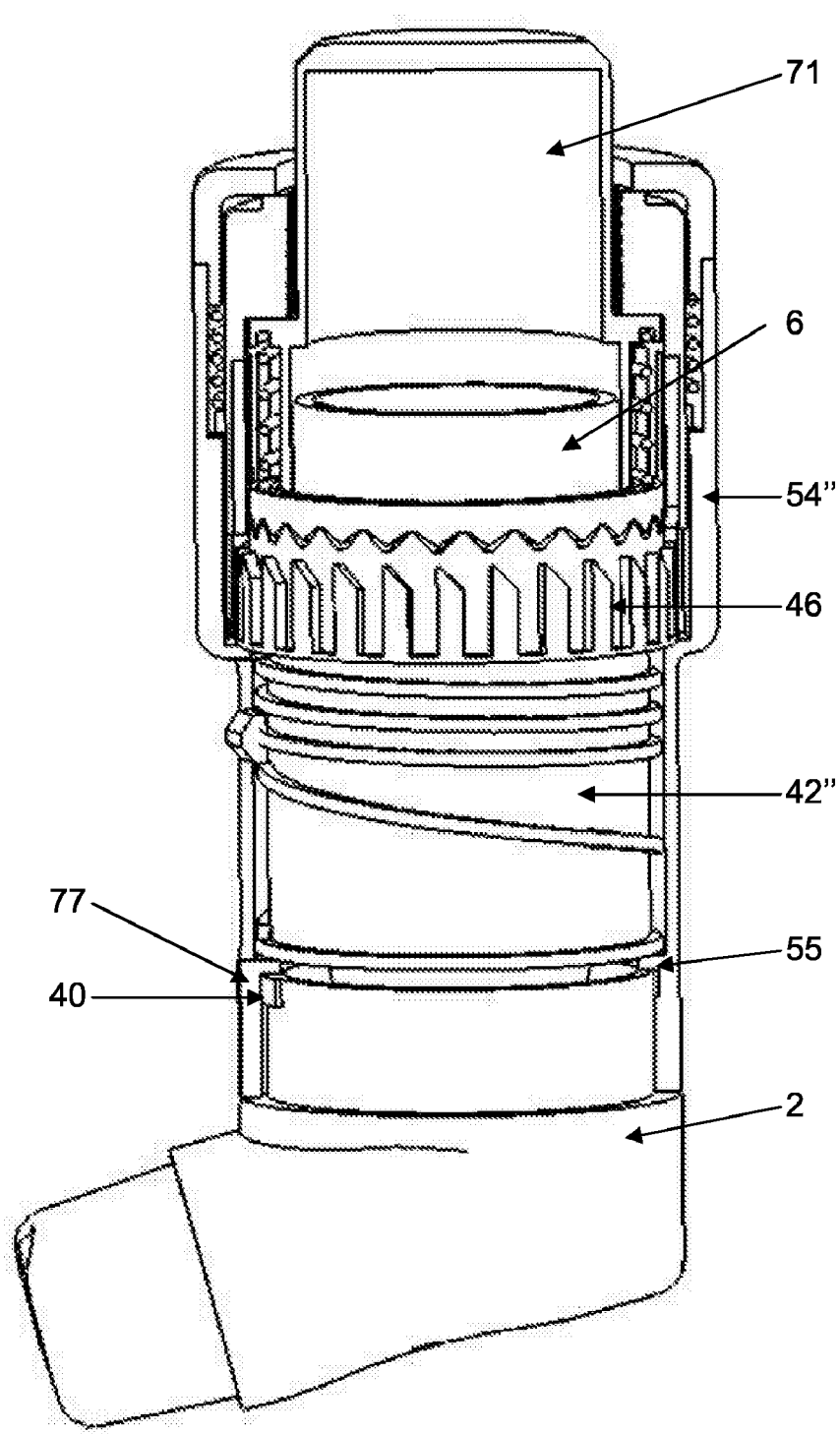
FIG. 15 illustrates the components of the dose counter device according to a third embodiment mounted on top of an inhaler in a non-activated state, partly seen in cross-section.

The driving means of the third embodiment, seen in FIG. 15, has thus accordingly been designated the reference number 42". The driving means 42" is adapted to be mounted inside the house 54". The difference between the driving means of the second embodiment and third embodiment, respectively, can be seen at the interior surface of the driving means wherein the distal end of the driving means 42" has a larger diameter than the rest of the driving means 42". Further, the driving means 42" is adapted to be mounted over the distal end of the inhaler housing 2 on a flange 55 at the proximal end of the house 54".

As in the second embodiment, the driving means 42" is adapted to be fitted inside the house 54". The difference, seen in FIG. 16, between the house of the second and the third embodiment, respectively, is that no inward protruding pins 62 are provided on the interior surface of the distal end of the house, that the distal part of the house has a larger diameter than the rest of the house 54", that a through hole is provided at its top, that a slot 76 is provided in the interior surface at the distal end of the house and that slots 77, seen in FIG. 15, are provided in the interior surface at the distal end of the house.

In the third embodiment, seen in FIG. 15, the housing 2 is provided with preferably two equally distributed outward protruding pins 40 abutting against the slots 77 of the house 54", instead of having those on the calibrating means 36. Further, in the third embodiment none calibrating means is required.

Figure 16:
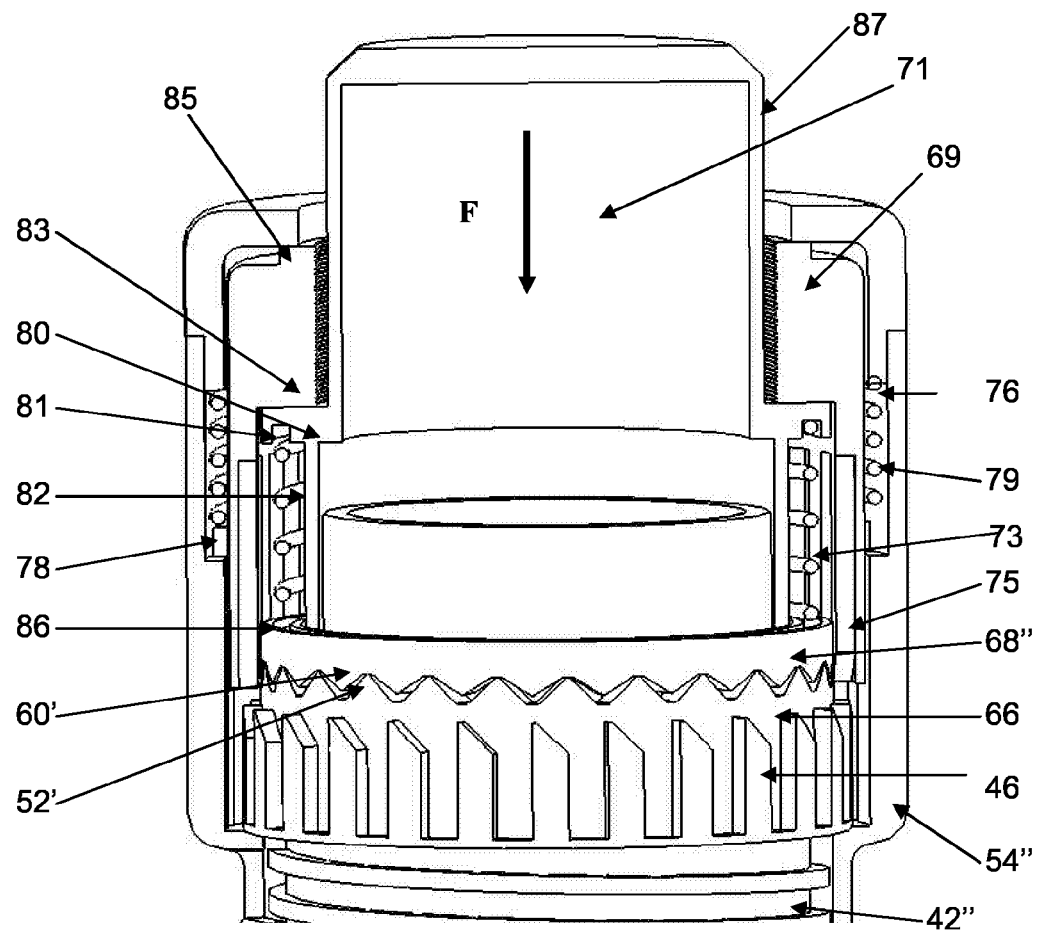
FIG. 16-20 illustrates the cooperation between the components of the dose counter device according to a third embodiment mounted on top of an inhaler and the driving means in four different subsequent stages for activation.

As seen in FIG. 16, an intermediate means 69 is provided at its top with a through hole wherein said through hole has a certain diameter and height. Said through hole may be provided with friction means as a ribbed interior surface or other types of engage means on its interior surface. Further, said intermediate means 69 is provided on its interior surface with an inward flange 83 and with inward protruding pins 75 having a bevelled edge that corresponds to the bevelled edge of the pins 46 on the driving means 42". The through hole of said intermediate means 69 has a slightly smaller diameter that the through hole of the house 54". An outward flange 85 at the top of the intermediate means 69 abuts against the interior surface of the house 54" wherein the edges of the through holes suit each other. Further, said intermediate means 69 is provided on its exterior surface with an outward protruding ledge or pins 78 that corresponds to the slot 76 of the house 54".

As seen in FIG. 16, an spring 79, preferably a helical steel spring is mounted in the slot 76 of the house 54" between the outward protruding ledge or pins 78 of the actuating means 69 and a flange of the slot 76 at its distal end. Further, the spring 79 may instead be mounted between the actuating means 69, surrounding the outward flange 85 at the top of the intermediate means 69 and the interior surface of the top of the house 54" (not shown).

Figure 18:
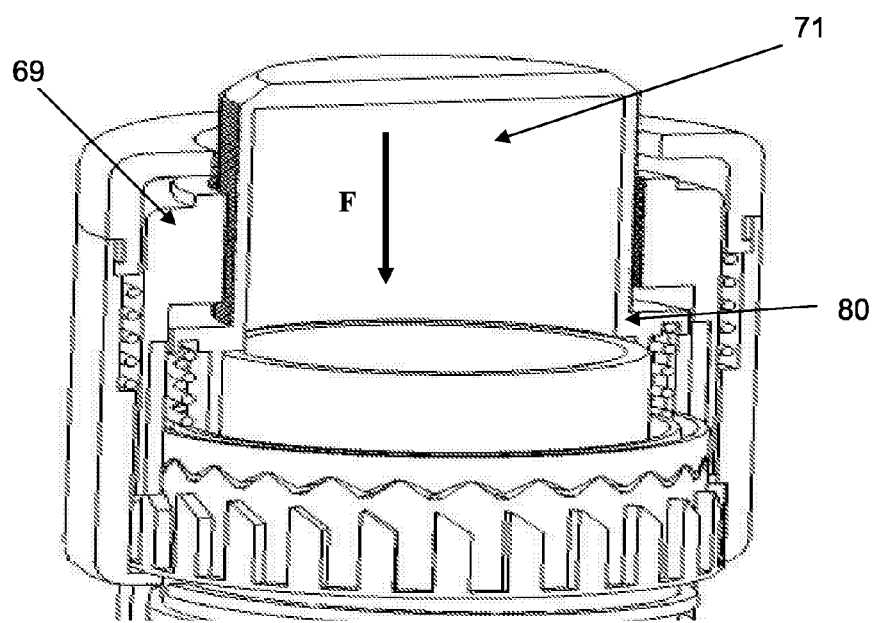

As seen in FIG. 16, an actuating means 71 is provided as a longitudinal sleeve 87 having bending walls of certain diameter and height. Said longitudinal sleeve 87 being of a flexible material may be provided with friction means as a ribbed exterior surface on its bending walls or with other types of engage means on the exterior surface of its bending walls, as seen in FIG. 18. Further, said actuating means 71 is arranged with an outward flange 80 having a slot 81 and a longitudinal extending sleeve 82 of certain diameter and height surrounding the canister 6. Further, said outward flange 80 abuts against the inward flange 83 of the intermediate means 69.

As seen in FIG. 16, a non-rotating means 68" is provided in the distal end of the interior of the house 54", overlaying the driving means 42" and the crown 66. The proximal edge of the non-rotating means is provided with downward protruding triangularly shaped teeth 60', which correspond to the teeth 52' of the driving means 42". The distal edge of the non-rotating means is provided with a slot 86.

The non-rotating means 68" is provided as a ring being depressed by a spring 73. The spring 73, preferably a helical steel spring is thus mounted between the slot 81 of the actuating means 71 and the slot 86 at the distal edge of the non-rotating means 68".

In the first and the second embodiments, the calibrating means 36 is adapted to be mounted over the distal end of the inhaler housing 2. This must be a well controlled mounting procedure so that the distance between the distal end of the calibrating means 36 and the distal end of the canister 6, is a well defined and predetermined distance, as indicated in FIG. 3 by the letter E. This is not required in the third embodiment, since the actuating means 71 interacts with the intermediate means 69 and performs the calibration.

Figure 17:
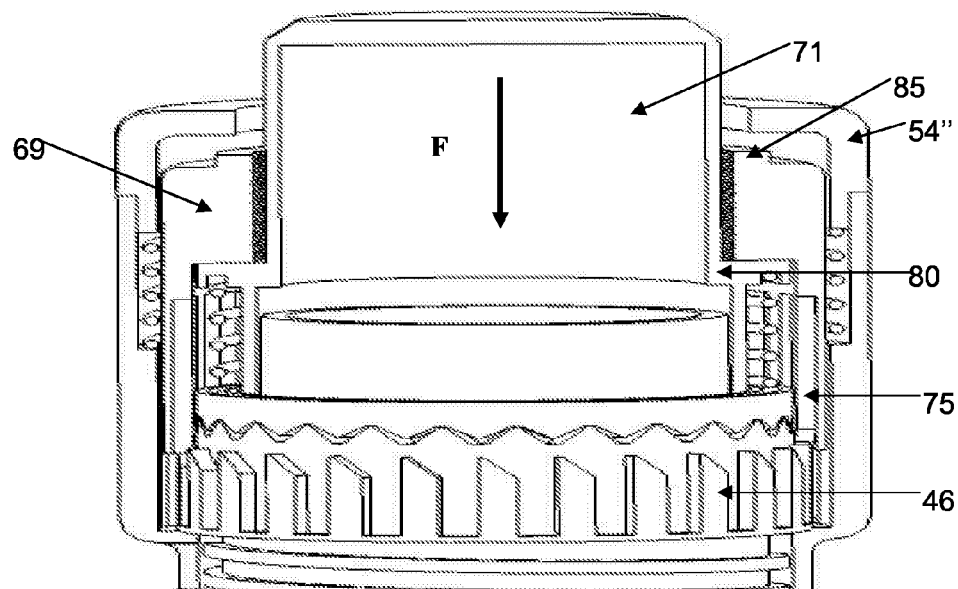
Figure 19:
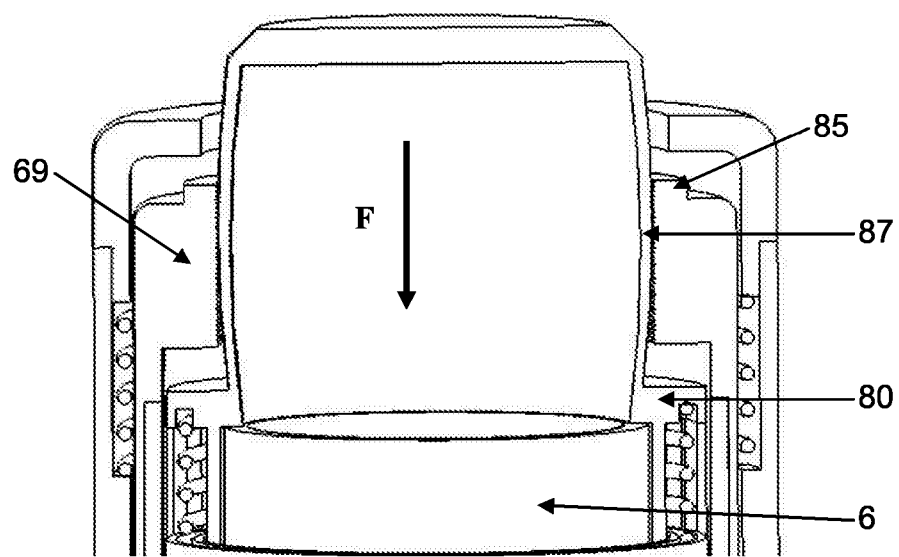
Figure 20:
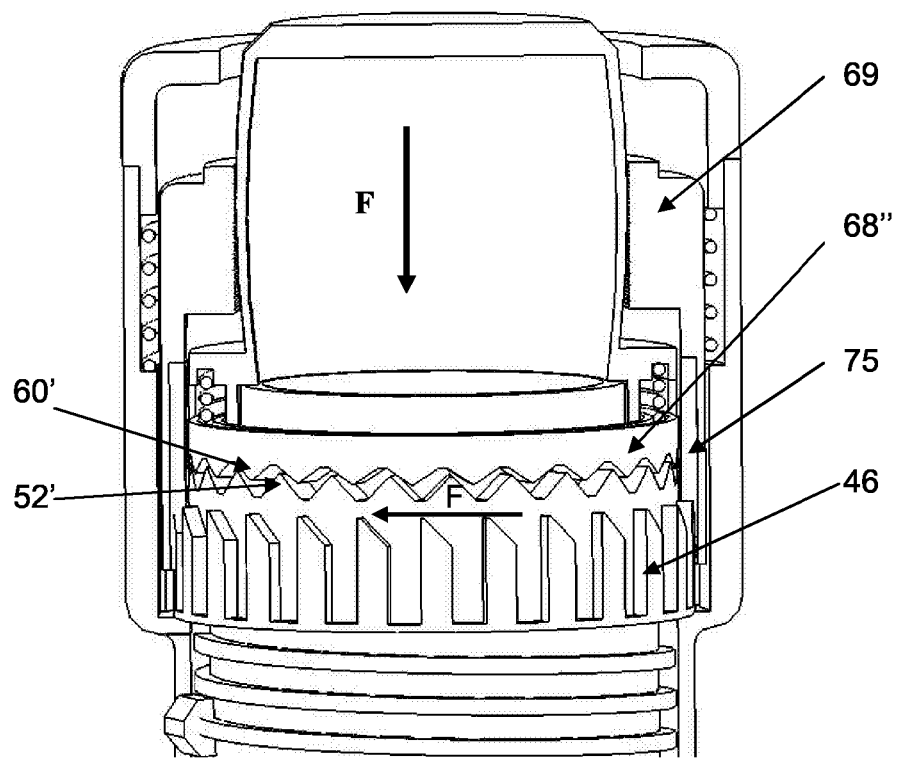

So, in the third embodiment when the actuating means 71 is urged downwards, the spring 73 will be depressed and the spring 79 will urge the intermediate means 69 to move downward until the bevelled edges of the pins 75 will make contact with the bevelled edges of the pins 46, as seen in FIG. 17. The outward flange 85 will come out of contact from the interior surface of the house 54" and the actuating means 71 will continue to move downward until the outward flange 80 makes contact with the distal edge of the canister. Then, the longitudinal sleeve 87 will bend its bending walls outwardly until its friction or engage means make contact with the friction or engage means of the intermediate means's through hole, as seen in FIG. 19. This contact or engagement, will urge the intermediate means 69 to continue its downward movement until the bevelled edges of the pins 75 will move along the bevelled edges of the pins 46 and urge the driving means 42" to rotate in the direction indicated by the arrow F in FIG. 20. The movement of the driving means to the left as seen in FIG. 20, will thus result in that a tip of a tooth 52' also will move to the left urging the spring-suspended non-rotating means 68" up towards the distal end of the inhaler.

The dose counter device is designed so that the distance that one tooth 52' has to move in order to for its tip to meet the tip of a tooth 60' is a known predetermined distance and that corresponds to a predetermined distance that the canister body then has moved towards the proximal edge of the inhaler. When a tip of a tooth 52', meets a tip of a tooth 60', the canister body has in this particular embodiment moved 1 mm towards the proximal end of the inhaler. This is due to the fact that when the user has pressed the canister downwards this particular distance, one can be pretty certain that he is to inhale a dose and that the downward movement of the canister was not as a result of general handling of the inhaler. Thus, when the two tips of the teeth 52', 60' meet, the tooth 52' will inevitably slide over the tooth tip 60' and the dose counter device has thus rotated one step and has accordingly registered a delivered dose, as described in connection with the first embodiment.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A dose counter device adapted for mounting on a distal end of an inhaler that includes an arrangement of at least a canister in an inhaler housing, a distal end of the canister protruding a distance from a distal end of the inhaler housing, the dose counter device comprising:
    means for registering a delivered dose, wherein the inhaler housing and the distal end of the canister interact with the registering means; and
    means for compensating for height dimension variations of the canister, of the registering means, and of the arrangement, wherein the compensating means is arranged to interact with the registering means, whereby erroneous counting of a delivered dose from the canister caused by height dimension variations of the canister, of the registering means, and of the arrangement is avoided;
    wherein the compensating means is adapted to be tightly mounted and not removably fitted over the distal end of the inhaler housing so that a distance between the distal end of the compensating means and the distal end of the canister is a determined distance, whereby a distance that the canister has to be displaced within the inhaler before a delivered dose is registered is accurately determined.

2. The dose counter device of claim 1, further comprising a driver and a house mounted over the compensating means.

3. The dose counter device of claim 2, wherein the house includes a flange adapted for contact with the distal end of the canister, outwardly protruding triangularly shaped teeth that correspond to teeth of the driver, and inwardly protruding pins having beveled edges that correspond to beveled edges of pins on the driver; and the house and the driver are adapted to urge the canister downward and to urge the driver to rotate one step and register a delivered dose.

4. The dose counter device of claim 3, wherein a distance that a tooth has to move for its tip to meet a tip of another tooth corresponds to a distance that the canister body then will have moved toward the proximal edge of the inhaler, and when the tips of the teeth meet, the tooth slides over the tip of the other tooth.

5. The dose counter device of claim 4, wherein teeth are provided in different configurations, whereby the driver is prevented from rotating in a wrong direction.

6. The dose counter device of claim 2, wherein the driver includes an upwardly protruding crown having equally distributed upwardly protruding triangularly shaped teeth which are arranged to interact with protruding triangularly shaped teeth of a non-rotating device when the house is pressed downward, whereby the canister is urged downward and the driver is urged to rotate one step and register a delivered dose.

7. The dose counter device of claim 6, wherein a distance that a tooth has to move for its tip to meet a tip of another tooth corresponds to a distance that the canister body then will have moved toward the proximal edge of the inhaler, and when the tips of the teeth meet, the tooth slides over the tip of the other tooth.

8. The dose counter device of claim 7, wherein teeth are provided in different configurations, whereby the driver is prevented from rotating in a wrong direction.

9. The dose counter device of claim 1, further comprising a driver, an actuator, and an intermediate device, wherein the driver, the actuator, and the intermediate device are adapted to fit inside a house; and the driver is mounted over the distal end of the inhaler housing on a flange at a proximal end of the house.

10. The dose counter device of claim 9, wherein the intermediate device is arranged to travel a longitudinal distance, when depressed, until it contacts the distal end of the canister, and to interact with the an actuator through springs and friction or an engagement device before a delivered dose is registered, whereby the intermediate device compensates automatically for height dimension variations of the canister, of the registering means, and of the arrangement.

11. The dose counter device of claim 10, wherein the driver includes an upwardly protruding crown having equally distributed upwardly protruding triangularly shaped teeth which are arranged to interact with protruding triangularly shaped teeth of a non-rotating device when the actuator is pressed downward, whereby the canister is urged downward and the driver is urged to rotate one step and register a delivered dose.

12. The dose counter device of claim 11, wherein a distance that a tooth has to move for its tip to meet a tip of another tooth corresponds to a distance that the canister body then will have moved toward the proximal edge of the inhaler, and when the tips of the teeth meet, the tooth slides over the tip of the other tooth.

13. The dose counter device of claim 12, wherein teeth are provided in different configurations, whereby the driver is prevented from rotating in a wrong direction.

14. The dose counter device of claim 1, wherein the house includes a flange adapted for contact with the distal end of the canister, outwardly protruding triangularly shaped teeth that correspond to teeth of the driver, and inwardly protruding pins having beveled edges that correspond to beveled edges of pins on the driver; and the house and the driver are adapted to urge the canister downward and to urge the driver to rotate one step and register a delivered dose.

15. The dose counter device of claim 14, wherein a distance that a tooth has to move for its tip to meet a tip of another tooth corresponds to a distance that the canister body then will have moved toward the proximal edge of the inhaler, and when the tips of the teeth meet, the tooth slides over the tip of the other tooth.

16. The dose counter device of claim 15, wherein teeth are provided in different configurations, whereby the driver is prevented from rotating in a wrong direction.

* * * * *